(12) United States Patent
Sakai et al.

(10) Patent No.: US 6,656,153 B1
(45) Date of Patent: Dec. 2, 2003

(54) BALLOON CATHETER

(75) Inventors: Kouichi Sakai, Kanagawa-ken (JP); Tetsuo Toyokawa, Kanagawa-ken (JP); Takahiro Iida, Kanagawa-ken (JP)

(73) Assignee: Nippon Zeon Co., LTD, Tokyo (JP)

( * ) Notice: Subject to any disclaimer, the term of this patent is extended or adjusted under 35 U.S.C. 154(b) by 0 days.

(21) Appl. No.: 09/508,193

(22) PCT Filed: Sep. 11, 1998

(86) PCT No.: PCT/JP98/04097

§ 371 (c)(1),
(2), (4) Date: Mar. 8, 2000

(87) PCT Pub. No.: WO99/13934

PCT Pub. Date: Mar. 25, 1999

(30) Foreign Application Priority Data

Sep. 12, 1997 (JP) ............................................. 9-267805

(51) Int. Cl.[7] ........................ A61M 29/00; A61M 5/178; A61M 25/01; A61M 25/02; A61M 25/04; A61M 25/06; A61M 25/08; A61M 25/082; A61M 25/085; A61M 25/088; A61M 25/09; A61M 25/095; A61M 25/098

(52) U.S. Cl. .............................. 604/99.04; 604/167.03; 604/164.13; 604/528; 606/194

(58) Field of Search ............................. 604/99.04, 264, 604/523, 528, 164.13, 533, 96.01, 1, 167.01–167.06; 600/488, 585; 606/192–194

(56) References Cited

U.S. PATENT DOCUMENTS

| | | | | |
|---|---|---|---|---|
| 3,853,127 A | * | 12/1974 | Spademan | 604/167.01 |
| 4,813,934 A | * | 3/1989 | Engelson et al. | 604/99.02 |
| 5,085,635 A | * | 2/1992 | Cragg | 604/102.03 |
| 5,171,221 A | * | 12/1992 | Samson | 604/913 |
| 5,304,198 A | * | 4/1994 | Samson | 600/585 |
| 5,324,259 A | * | 6/1994 | Taylor et al. | 604/99.04 |
| 5,437,632 A | * | 8/1995 | Engelson | 604/523 |
| 5,873,835 A | * | 2/1999 | Hastings et al. | 600/488 |
| 5,882,334 A | * | 3/1999 | Sepetka et al. | 604/164.08 |
| 6,004,279 A | * | 12/1999 | Crowley et al. | 600/433 |
| 6,017,323 A | * | 1/2000 | Chee | 604/249 |
| 6,074,407 A | * | 6/2000 | Levine et al. | 606/194 |
| 6,231,543 B1 | * | 5/2001 | Hegde et al. | 604/96.01 |
| 6,254,588 B1 | * | 7/2001 | Jones et al. | 604/525 |

FOREIGN PATENT DOCUMENTS

| | | |
|---|---|---|
| JP | 3-502051 | 5/1991 |
| JP | 60-500900 | 6/1995 |

* cited by examiner

Primary Examiner—Brian L. Casler
Assistant Examiner—Catherine Serke
(74) Attorney, Agent, or Firm—Armstrong, Westerman & Hattori, LLP

(57) ABSTRACT

A balloon catheter of the present invention has an outer tube having a first lumen inside it. At the distal end of the outer tube is connected the proximal end of the balloon portion so that a balloon space is formed inside it, the distal end of the balloon portion is joined to a cylindrical front tip portion, and pressurized fluid is introduced into and released from the balloon space through the first lumen of the outer tube so as to make the balloon portion expand or contract. Inside the first lumen of the outer tube is arranged an inner tube having a second lumen freely slidable in the axial direction. The distal end of the inner tube projects out from the distal end of the outer tube and is detachably attached to the front tip portion. The balloon catheter of the present invention may have a guidewire detachably attached to the front tip portion rather than providing the inner tube.

22 Claims, 9 Drawing Sheets

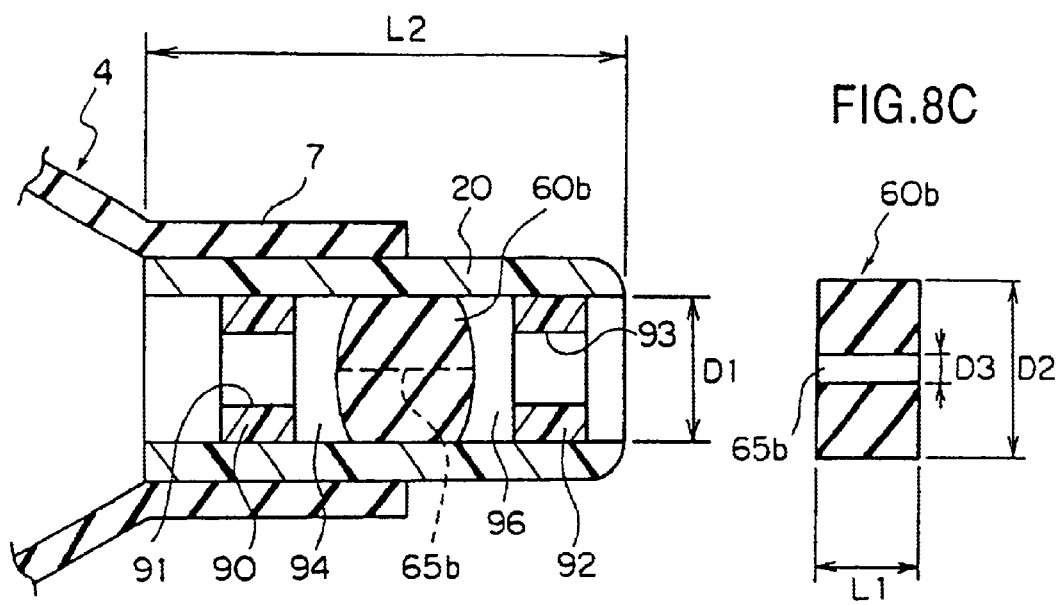
FIG.8A
FIG.8C
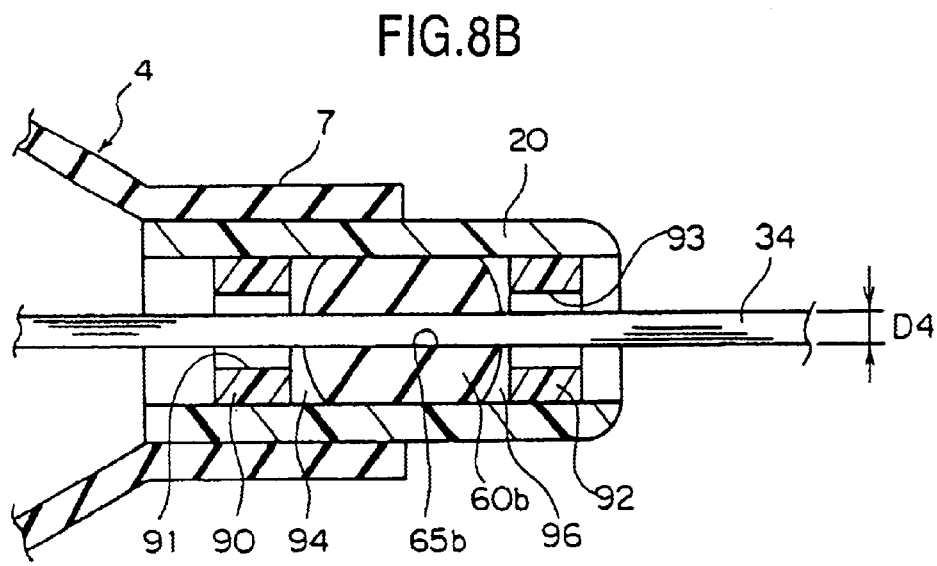
FIG.8B

BALLOON CATHETER

TECHNICAL FIELD

IABP is a method for treatment when the heart functions decline due to cardiac insufficiency etc. and is designed to assist heart functions by the insertion of a balloon catheter in the aorta and expanding and contracting the balloon portion along with the beating of the heart.

BACKGROUND ART

IABP is a method for treatment when the heart functions decline due to cardiac insufficiency etc. and is designed to assist heart functions by the insertion of a balloon catheter in the aorta and expanding and contracting the balloon portion along with the beating of the heat.

Various balloon catheters used for such IABP have been proposed (Japanese Unexamined Patent Publication (Kokai) No. 63-206255, Japanese Unexamined Patent Publication (Kokai) No. 62-11456, etc.)

In such balloon catheters, there is known a so-called double lumen type balloon catheter in which the balloon catheter is inserted into a blood vessel along a guidewire so as to enable the balloon portion to be guided to a predetermined position close to the heart in the arterial blood vessel. This balloon catheter has an inner tube arranged inside an outer tube forming the catheter tube. The lumen of the inside of the outer tube serves as a flow channel for a shuttle gas for causing the balloon portion to expand or contract, while the lumen of the inner tube serves as a through hole for the guidewire for guiding the balloon portion to the predetermined position near the heart in the artery.

In such a balloon catheter having an inner tube, however, there is the following problem. That is, the outer tube forming the catheter tube is supposed to be inserted inside the artery of the patient, so considering the discomfort to the patient, in particular the circulation of the blood from the point of insertion to the tissue at the terminal side, preferably should be as small in outer diameter as possible.

If the outer diameter of the outer tube is small, however, the cross-section of the flow channel of the lumen formed inside it becomes small. The inside of the outer tube also has the inner tube disposed in it so the actual cross-sectional area of the flow channel for the circulation of the gas is reduced even more. To enlarge the actual cross-sectional area of the flow channel in the lumen of the outer tube, it is preferable that the outer diameter of the inner tube also be small. The lumen of the inner tube, however, has the guidewire inserted through it, so there is a limit to how small the outer diameter of the inner tube can be made.

The lumen of the outer tube other than the cross-section of the inner tube is passed through by the gas for causing the expansion and contraction of the balloon portion. If the outer diameter of the outer tube is made small, the cross-sectional area of the flow channel of the lumen becomes increasingly small, the resistance of the flow channel increases, the response of expansion and contraction of the balloon portion driven by the gas becomes poorer, and consequently a timing lag of the expansion or contraction is liable to occur and assisting action to the heart can not be achieved effectively.

The period of expansion and contraction of the balloon portion is, for example if the heart beat is 100 beats per minute, a period of 0.6 second. The gas passes back and forth inside the lumen of the outer tube within a time shorter than that period, so the smaller the resistance of the flow channel the better.

As explained above, however, the inner tube is placed inside the lumen of the outer tube and there are limits to how small the outer diameter of the inner tube can be made. Further, there are limits to how small the outer diameter of the outer tube can be made.

Therefore, in the prior art, there was no choice but to set the outer diameter of the outer tube forming the catheter tube as large as possible within a range not causing a remarkable increase in the discomfort to the patient. In order to obtain a satisfactory level of response in the expansion and contraction of the balloon portion, the discomfort to the patient was unavoidably increased to a certain extent.

DISCLOSURE OF THE INVENTION

The present invention was made in consideration of this actual situation and has as its object the provision of an innovative balloon catheter which enables an improvement in the response of expansion and contraction of the balloon portion despite being able to reduce the outer diameter of the outer tube forming the catheter tube and alleviating the discomfort to the patient.

To achieve the above object, the first balloon catheter according to the present invention comprises an outer tube having a first lumen inside the outer tube, a balloon portion having a proximal end of the balloon portion joined to a distal end of the outer tube and a distal end of the balloon portion joined to a tubular shaped front tip portion in order to form a balloon space inside the balloon portion, into which a pressurized fluid is introduced and released from through the first lumen of the outer tube to give an expanded and contracted state, and an inner tube having a second lumen inside the inner tube extending inside the first lumen of the outer tube to freely slide in the axial direction, projecting out from the distal end of the outer tube, and detachably attached to the front tip portion.

The second balloon catheter according to the present invention comprises an outer tube having a first lumen inside the outer tube, a balloon portion having a proximal end of the balloon portion joined to a distal end of the outer tube and a distal end of the balloon portion joined to a tubular shaped front tip portion in order to form a balloon space inside the balloon portion, into which a pressurized fluid is introduced and released from through the first lumen of the outer tube to give an expanded and contracted state, and a valve element through which a guidewire extending inside the first lumen of the outer tube to be freely slidable in the axial direction can be passed in a detachable manner, the valve element being attached to the front tip portion so as to maintain the inside of the balloon portion sealed in both the state with the guidewire attached and the state with the guidewire not attached to the valve element. Note that in the present invention, the "guidewire" is not particularly limited in material. The term is used in the sense including a member comprised of a rod made of a synthetic resin in addition to an ordinary metal guidewire.

In the present invention, the cross-sectional shape of the outer tube is not particularly limited. It may be circular or polylateral in shape, but a circular shape is preferable. At the inside of the outer tube is formed a lumen along the longitudinal direction.

In the present invention, the balloon portion is formed by a tubular film in which a balloon space is formed. In the expanded state, it has an outer diameter larger than the outer tube. In the expanded state, the cross-sectional shape of the balloon portion is not particularly limited and may be circular or polylateral, but it is preferably circular.

At the inside of the tubular front tip portion is preferably attached a valve element sealing the balloon space inside the balloon portion from the outside of the balloon portion. To this valve element, preferably a distal end of the inner tube (or guidewire) is detachably attached. This valve element can seal the balloon space at the inside of the balloon portion from the outside of the balloon portion both in a state with the distal end of the inner tube (or guidewire) attached to the valve element and in a state with the inner tube (or guidewire) detached. The valve element is not particularly limited. It is not limited to a duckbill valve or other hemostatic valve normally used as a medical part. A three-way cock valve, compression spring valve, water absorbing polymer slit valve, etc. may also be mentioned.

The valve element preferably used in the present invention is formed with a tight-fit hole. In the state with the distal end of the inner tube inserted into the tight-fit hole, the clearance with the inner tube (or guidewire) is sealed. In the state with the inner tube (or guidewire) detached from the tight-fit hole, the tight-fit hole closes to enable the balloon space at the inside of the balloon portion to be sealed from the outside of the balloon portion.

Preferably, the maximum outer diameter of the valve element is larger than the inside diameter of the front tip portion in the state before the valve element is attached to the inside of the front tip portion, and the valve element is compressed and elastically deformed and attached to the inside of the front tip portion in the state with the tight-fit hole closed.

Preferably, in the state with the distal end of the inner tube (or guidewire) inserted into the tight-fit hole of the valve element, the tight-fit hole stretches and an extra clearance space for elastic deformation of the valve element in the axial direction is formed inside the front tip portion.

To create this extra clearance space inside the front tip portion, preferably the inside of the front tip portion is provided with stopper members positioned at both sides of the valve element in the axial direction. The stopper members are constructed to allow passage of the inner tube (or guidewire).

The Shore A hardness of the valve element is preferably not more than 30, more preferably not more than 20, particularly not more than 15 and may be even less than 5. The Shore A hardness is measured based on JIS K6253.

The breaking elongation of the valve element is preferably 300 to 1000%, particularly preferably 500 to 800%. The breaking elongation is measured based on JIS K7311.

The compression modulus of elasticity of the valve element is preferably 0.01 to 0.30 kg/cm$^2$, more preferably 0.05 to 0.15 kg/cm$^2$. The compression modulus of elasticity is measured based on JIS K7208.

The front tip portion is preferably comprised of a member which can elastically deform to the outside in the radial direction.

The front tip portion preferably is provided with a pressure sensor for measuring the blood pressure etc.

The balloon catheter according to the present invention preferably further comprises a supporting rod member having a distal end joined to the front tip portion and extending inside the balloon portion and the outer tube in the axial direction separate from the inner tube (or guidewire). This supporting rod member is preferably comprised of a tube. Inside the tube is preferably passed or buried wiring from the pressure sensor.

Preferably the proximal end of the outer tube is connected to a connector and the proximal end of the inner tube (or guidewire) is detachably attached to the connector. The proximal end of the supporting rod member is preferably connected to the connector. A terminal takeout portion for the wiring passed through or buried in the tubular supporting rod member is preferably formed in the connector.

In the first balloon catheter according to the present invention, since an inner tube is attached along the axial direction inside the balloon portion and the outer tube when inserting the balloon catheter into a blood vessel or other body cavity of the patient, by passing a guidewire inside the second lumen of the inner tube, it is possible to adroitly guide the balloon portion of the balloon catheter to a predetermined position inside the body cavity.

By pulling out the inner tube from the proximal end side of the balloon catheter positioned at the outside of the body after positioning the balloon portion at the predetermined position inside the body cavity, the inner tube no longer exists inside the outer tube forming the catheter tube. Around this time, if necessary, the guidewire may also be pulled out from the proximal end side of the balloon catheter and then the balloon catheter used for treatment.

Note that in the second balloon catheter of the present invention, there is no inner tube attached from the very start. Therefore, when inserting the second balloon catheter into a blood vessel or other body cavity of a patient, by passing the guidewire along the inside of the first lumen of the outer tube and the balloon portion, it is possible to adroitly guide the balloon portion of the balloon catheter to a predetermined position inside the body cavity. Next, in accordance with need, the guidewire is pulled out from the proximal end side of the balloon catheter and the balloon catheter is used for treatment. In this state, both the first balloon catheter and the second balloon catheter according to the present invention become the same.

In this state, in the first and second balloon catheters of the present invention, the cross-sectional area of the flow channel of the first lumen of the outer tube forming the catheter tube becomes larger by the amount of the removal or nonprovision of the inner tube. As a result, the cross-section of the flow channel for feeding pressurized fluid inside the balloon portion becomes larger and the response of expansion and contraction of the balloon portion is remarkably improved. Further, this means that the same or better response characteristics of expansion and contraction of the balloon portion as in the prior art can be obtained even if making the outer diameter of the outer tube forming the catheter tube smaller than the conventional balloon catheter.

This point is also preferable since if the outer diameter of the outer tube forming the catheter tube can be made smaller, the discomfort to the patient can be alleviated.

BRIEF DESCRIPTION OF THE DRAWINGS

FIGS. 8A and 8B are schematic sectional views of key parts of a balloon catheter according to another embodiment of the present invention;

FIG. 8C is a sectional view of key parts of the valve element shown in FIGS. 8A and 8B;

BEST MODE FOR CARRYING OUT THE INVENTION

The present invention will be explained in detail below based on the embodiments shown in the figures.

First Embodiment

Figure 1:
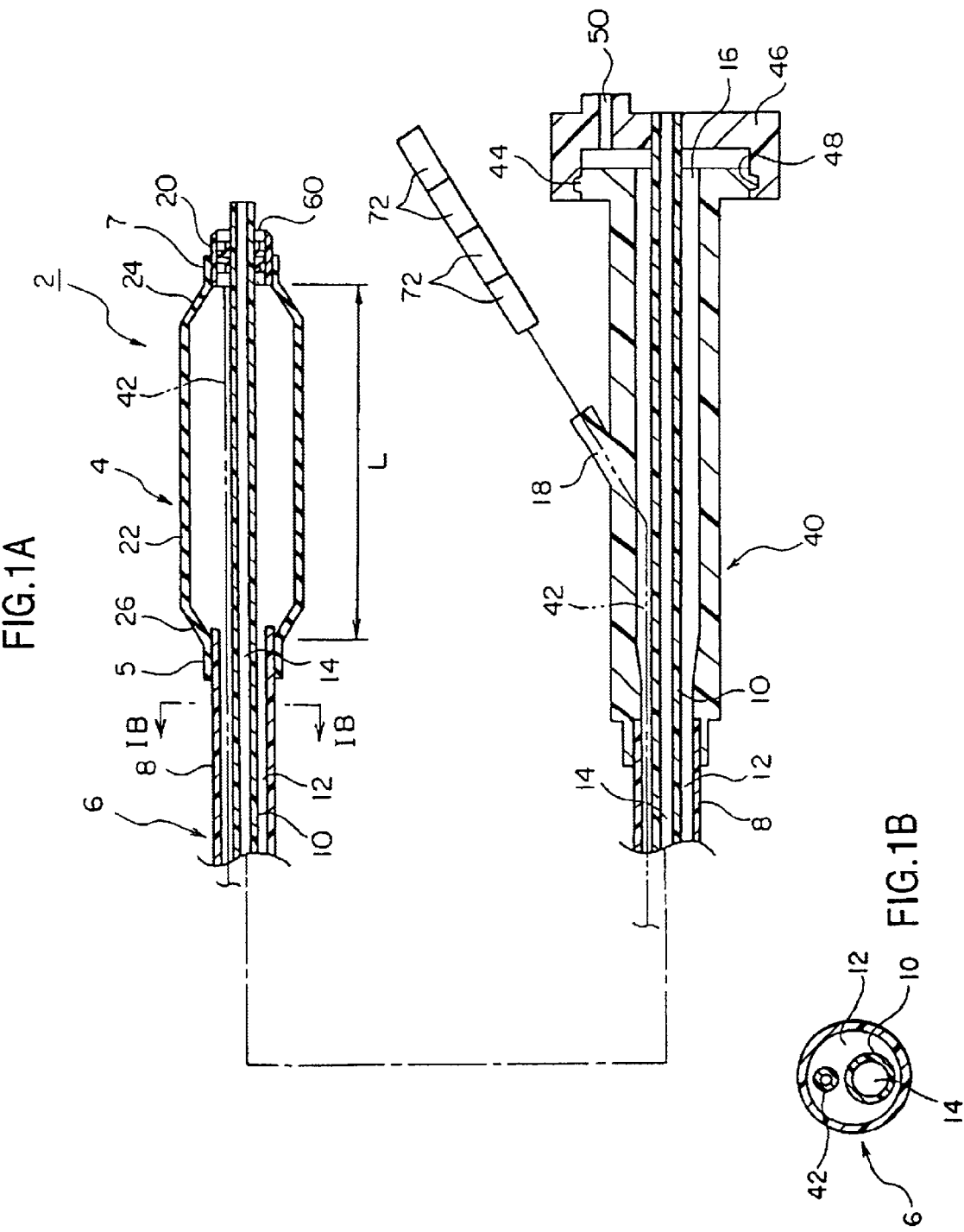
FIG. 1A is a schematic sectional view of a balloon catheter according to a first embodiment of the present invention.
FIG. 1B is a sectional view along IB—IB shown in FIG. 1A.

The balloon catheter 2 according to the first embodiment shown in FIG. 1 is one used for IABP and has a balloon portion 4 which expands and contracts along with the beating of the heart. The balloon portion 4 is preferably comprised of a tubular balloon film 22 of a film thickness of 50 to 150 μm and has a balloon space formed inside it.

This is because if the film thickness is less than 50 μm, the film is inferior in strength, while if over 150 μm, the expansion might not be smoothly possible. In the present embodiment, the shape of the balloon film 22 in the expanded state is that of a cylindrical tube, but the present invention is not limited to this and may be a polylateral tube in shape as well.

The IABP balloon film 22 is preferably made of a material superior in flexural fatigue resistance. For example, it is formed by a material such as polyurethane, silicone, soft polyethylene, soft polyamide, or soft polyester. In particular, one formed by polyurethane is suitable in that it is high in ability to suppress the occurrence of thrombus and high in abrasion resistance as well. The outer diameter and length of the balloon film 22 are determined in accordance with the inside volume of the balloon film 22, which has a large effect on the effect of assisting heart functions, and the inner diameter of the arterial blood vessel. For example, when the inside volume of the balloon portion 4 is 25 to 65 cc, the outer diameter D of the balloon portion 4 when expanded is preferably 10 to 30 mm, more preferably 15 to 25 mm, while the length L of the balloon portion 4 (see FIG. 1) is preferably 90 to 300 mm, more preferably 110 to 250 mm. The length L of the balloon portion 4 is defined by the length from the portion connected to the distal end of the catheter tube 6 to the portion connected to the distal end of the front tip portion 20.

The method of production of the balloon film 22 according to this embodiment is not particularly limited, but for example it is possible to mention the method of dipping a mold for forming the balloon film in a molding solution, forming a resin film on the outer circumference of the mold, then drying and removing the film from the mold (dipping method). Further, there is the method of blow molding a parison so as to form the balloon film (blow molding method).

At the distal end of the balloon film 22 is formed a distal end side taper 24 forming a thin tip. The extreme distal end 7 is attached to the outer circumference of the distal end of the front tip portion 20 by means of such as heat bonding or adhesion.

The front tip portion 20 is comprised of a short cylindrical tube and for example is made of a short tube of a synthetic resin such as polyurethane, polyamide, and polyester or metal. The outer diameter of the front tip portion is not particularly limited, but is preferably about 1.0 to 3.0 mm, while the inner diameter is preferably about 0.5 to 2.5 mm.

At the proximal end of the balloon film 22 is formed a proximal end side taper 26 forming a thin tip. The extreme proximal end 5 is joined to the distal end of the outer tube 8 forming the catheter tube 6. The catheter tube 6 forms a double-tube structure comprised of the outer tube 8 and the inner tube 10. A first lumen 12 is formed between the outer tube 8 and the inner tube 10. At the inside of the inner tube 10 is formed a second lumen 14 not communicating with the inside of the balloon film 22 and the first lumen 12 formed at the inside of the catheter tube 6.

Pressurized fluid is introduced into and released from the inside of the balloon film 22 through the first lumen 12 formed inside the double-lumen catheter tube 6 so as to make the balloon film 22 expand or contract. The balloon film 22 and the outer tube 8 are joined by means of heat bonding or adhesion with an adhesive such as an ultraviolet curing resin.

The distal end of the inner tube 10 projects outward from the distal end of the outer tube 8. The inner tube 10 is inserted inside the balloon film 22 and the outer tube 8 to freely slide in the axial direction. The proximal end of the inner tube 10 is detachably attached to a later explained connector 40.

The inner tube 10 of the catheter tube 6, as explained later, is used for adroitly guiding the balloon portion 4 to a predetermined position inside the artery by inserting a guidewire inside the second lumen 14. When inserting the balloon catheter 2 into a blood vessel or other body cavity, the balloon film 22 forming the balloon portion 4 is folded and wound around the outer circumference of the inner tube 10 and supporting rod member 42. Details on the supporting rod member 42 will be given later.

The inner tube 10 shown in FIG. 1 may for example be formed by the same material as the outer tube 8, i.e., may be made of a synthetic resin tube of polyurethane, polyvinyl chloride, polyethylene, polyamide, or polyimide or a metal spring reinforced tube or stainless steel thin tube. Note that as a reinforcing member, it is also possible to use a stainless steel wire, nickel-titanium alloy wire, etc.

The inner diameter of the inner tube 10 is not particularly limited so long as it is one which enables the guidewire to be passed through the tube. For example, it is 0.15 to 1.5 mm, preferably 0.5 to 1 mm. The thickness of the inner tube 10 is preferably 0.1 to 0.4 mm. If less than 0.1 mm, the tube is inferior in strength, while if over 0.4 mm, the outer diameter of the inner tube 10 becomes too large, which is not desirable. The outer diameter of the inner tube 10 is preferably 0.3 to 2.5 mm, particularly preferably 0.5 to 1.5 mm.

The total length of the inner tube 10 is determined according to the axial length of the balloon catheter 2 inserted into the blood vessel etc. While not particularly limited, it is for example 500 to 1200, preferably about 700 to 1000 mm.

The outer tube 8 of the double-lumen catheter tube 6 is preferably made of a material having a certain degree of flexibility. For example, a polyethylene, polyethylene terephthalate, polypropylene, ethylene-propylene copolymer, ethylene-vinyl acetate copolymer, polyvinyl chloride (PVC), cross-linking type ethylene-vinyl acetate copolymer, polyurethane, polyamide, polyamide elastomer, polyimide, polyimide elastomer, silicone rubber, natural rubber, etc. may be used. Preferably, the tube is made of a polyurethane, polyethylene, polyamide, or polyimide. The outer diameter of the outer tube 8 of the catheter tube 6 may be uniform in the axial direction, but may also be formed to have a step portion midway or a taper so that the diameter is smaller near the balloon film 22 side and larger at the rest of the portion (proximal end side). By making the cross-sectional area of the flow channel of the first lumen 12 larger, it is possible to improve the response of expansion and contraction of the balloon film 22.

The inner diameter of the outer tube 8 of the catheter tube 6 is preferably 1.0 to 3.0 mm, more preferably 1.5 to 2.6 mm. Further, the thickness of the outer tube 8 is preferably 0.05 to 0.4 mm. If less than 0.05 mm, the tube is inferior in strength, while if over 0.4 mm, the outer diameter of the tube becomes too large and the operating property becomes poor. Further, the outer diameter of the outer tube 8 is preferably 1.3 to 3.3 mm, particularly preferably 1.8 to 3.0 mm. The clearance with the outer diameter of the inner tube 10 inserted into the first lumen of the outer tube 8 may be close to 0. This is because when introducing or releasing pressurized fluid into or from the inside of the balloon portion 4 through the first lumen 12 of the outer tube 8, the inner tube 10 is removed and therefore a sufficient cross-sectional area of the flow channel is secured. In the present embodiment, the length of the outer tube 8 is preferably about 300 to 800 mm.

At the proximal end of the outer tube 8 of the double-lumen catheter tube 6 is connected a connector 40 which will be placed at the outside of the body of the patient. The connector 40 formed separate from the outer tube 8 of the catheter tube 6 is fixed to it by means of such as heat bonding or adhesion. The connector 40 is formed with a port 16 for introducing or releasing pressurized fluid to or from the first lumen 12 of the catheter tube 6 and the balloon film 22 and a terminal takeout portion 18. The port 16 is arranged straight along the longitudinal direction inside the connector 40. The connector 40 is for example made of a thermoplastic resin such as a polycarbonate, polyamide, polysulfone, polyacrylate, or methacrylate-butylene-styrene copolymer.

At the outer circumference of the flange of the port 16 is formed a male lure fitting 44. The male lure fitting 44 has a female lure fitting 48 of a cap 46 detachably attached to it. The cap 46 is for example made of a material the same as the connector.

At the center of the cap 46 is heat bonded or adhered the proximal end of the inner tube 10 so that the proximal end of the second lumen 14 of the inner tube 10 opens there. The cap 46 is formed with a negative pressure introduction port 50. The negative pressure introduction port 50 is designed to enable a negative pressure generator to be connected to it through a check valve. Before introducing the balloon catheter 2 into a blood vessel, negative pressure is introduced from the negative pressure introduction port 50 through the port 16 and the first lumen 12 to make the inside of the balloon portion 4 a negative pressure and thereby make the balloon film 22 fold around the inner tube 10 and the supporting rod member 42 and reduce the outer diameter near the balloon portion 4.

Figure 3:
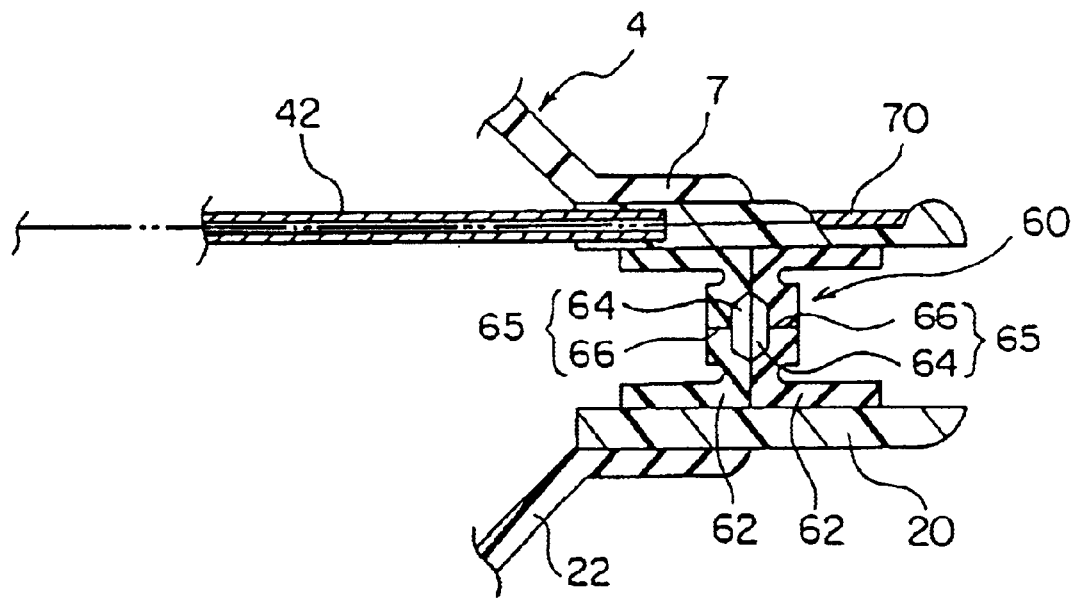
FIG. 3 is a sectional view of key parts showing details of the front tip portion of the balloon catheter shown in FIG. 1.

In this embodiment, as shown in FIG. 3, the inside of the front tip portion 20 has attached to it a valve element 60 for sealing the balloon space at the inside of the balloon portion from the outside of the balloon portion 4. The distal end of the inner tube 10 is detachably attached as shown in FIG. 1 so as to pass through the center of the valve element 60. In the state shown in FIG. 1, the second lumen 14 of the inner tube 10 communicates with the inside of the blood vessel through the distal end opening of the inner tube 10.

The valve element 60, as shown in FIG. 3, is a member that blocks the inside through hole of the front tip portion 20 so as to seal the inside through hole. That is, in the state where pressurized fluid is introduced inside of the balloon portion 4, leakage of the fluid to the outside is prevented. Further, in the state where pressurized fluid is released from the inside of the balloon portion 4, blood is prevented from entering into the balloon portion 4 through the through hole of the front tip portion 20. Further, as shown in FIG. 1, the distal end of the inner tube 10 is made to be able to be detachably attached so as to pass through the center oft he valve element 60. Even in the state shown in FIG. 1, the inside space of the balloon portion 4 is sealed from the outside.

The valve element 60 providing this value action is not particularly limited, but in the present embodiment use is made of a combination of the medical use valve elements (valve components) as shown in for example Japanese Patent Application No. 9-155968 back to back. The valve components 62 forming the valve element 60 are formed at their centers with tight-fit holes 65 through which the inner tube 10 is able to be inserted while maintaining a liquid seal. In the present embodiment, the tight-fit hole 65 is comprised of a through hole 64 and a slit 66.

The slit 66 is a Y-shaped or cross-shaped slit. The inside of the slit 66 is designed to communicate with the through hole 64. In the state with the inner tube 10 passed through the slit 66 and the state with the tube pulled out, liquid from the slit 66 side is prevented from being communicated with. The inner diameter of the through hole 64 is preferably designed to be smaller than the inner tube 10 which is inserted through the through hole 64, specifically is preferably 0.3 to 1.3 mm or so. In the present embodiment, the valve components 62 are comprised of silicone rubber.

As shown in FIG. 3, in the present embodiment, the extreme distal end 7 of the balloon portion 4 is affixed to the outer circumference at the proximal end side of the front tip portion 20, and a pressure sensor 70 for measuring the nearby blood pressure is buried in the outer circumference of the distal end side of the front tip portion 20. To take out the pressure detected by the pressure sensor 70 to the outside, the pressure sensor 70 normally has at least four wires connected to it. These wires are designed to pass through the inside of the tube-shaped supporting rod member 42 affixed to the proximal end side of the front tip portion 20. The supporting rod member 42 provides support in the longitudinal direction to the balloon catheter 2, in particular the balloon portion 4, after the inner tube 10 is pulled out and for example is made of a metal tube of a nickel alloy or titanium alloy or stainless steel. The outer diameter of the supporting rod member 42 is sufficiently smaller than the outer diameter of the inner tube 10, preferably 0.2 to 0.8 mm, more preferably 0.4 to 0.6 mm. When the supporting rod member 42 is a tube shape, the inner diameter of the tube is preferably 0.1 to 0.6 mm, particularly preferably 0.2 to 0.4 mm.

The proximal end of the supporting rod member 42, as shown in FIG. 1, is affixed near the terminal takeout portion 18 of the connector 40. The wires for the pressure sensor 70 passed through the inside through hole of the supporting rod member 42 are led out through the terminal takeout portion 18 of the connector 40 to outside of the connector and connected to a terminal 72 designed for electrical connection with another apparatus.

To provide IABP treatment using the balloon catheter 2 according to the present embodiment, first the balloon catheter 2 in the state shown in FIG. 1 is prepared. That is, the cap 46 is attached to the port 16 of the connector 40 in the state before IABP driving. Before introducing the balloon catheter 2 into the blood vessel, negative pressure is introduced from the negative pressure introduction port 50 of the connector 40 so as to make the inside of the balloon portion 4 a negative pressure through the port 16 and the first lumen 12 and thereby make the balloon film 22 fold around the inner tube 10 and the supporting rod member 42 and reduce the outer diameter near the balloon portion 4.

Figure 4:
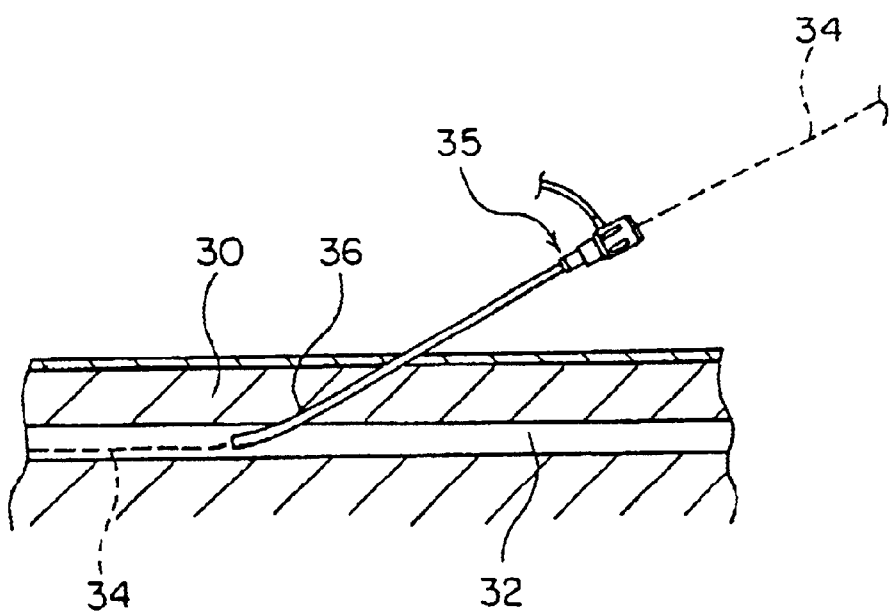
FIG. 4 is a schematic view of the state of insertion of the balloon catheter according to the present embodiment into a blood vessel.

Next, as shown in FIG. 4, a centesis needle comprised of a not shown outer needle (cannula) and inner needle is inserted into the skin 30 of the patient so that the front end thereof is positioned inside a blood vessel 4. Next, the inner needle is pulled out leaving the outer needle (cannula) and the guidewire 34 is inserted into the blood vessel 32 from the hole made by the removal of the inner needle.

The guidewire used is normally one with an outer diameter of 0.2 to 1.2 mm, preferably 0.4 to 0.9 mm and a length of 700 to 2000 mm, preferably 1000 to 1600 mm, made of stainless steel or a nickel-titanium alloy coated, when necessary, with a fluororesin or urethane resin etc.

Next, the outer needle is pulled out along the inserted guidewire 34, then the guidewire 34 is passed into a dilator and the front end of a catheter tube inserter comprised of an introducer 35 and the dilator (not shown) is inserted along the guidewire 34 into the incision 36 of the blood vessel.

When inserting the front end of the catheter tube inserter comprised of the introducer 35 and the dilator, as shown in FIG. 4, into the incision 36 of the blood vessel, the tapered front end formed at the front end of the dilator pushes wider the incision 36 of the blood vessel. By further pushing the front end of the catheter tube inserter inside, the front end of the introducer 35 is also inserted into the blood vessel 32.

Figure 2:
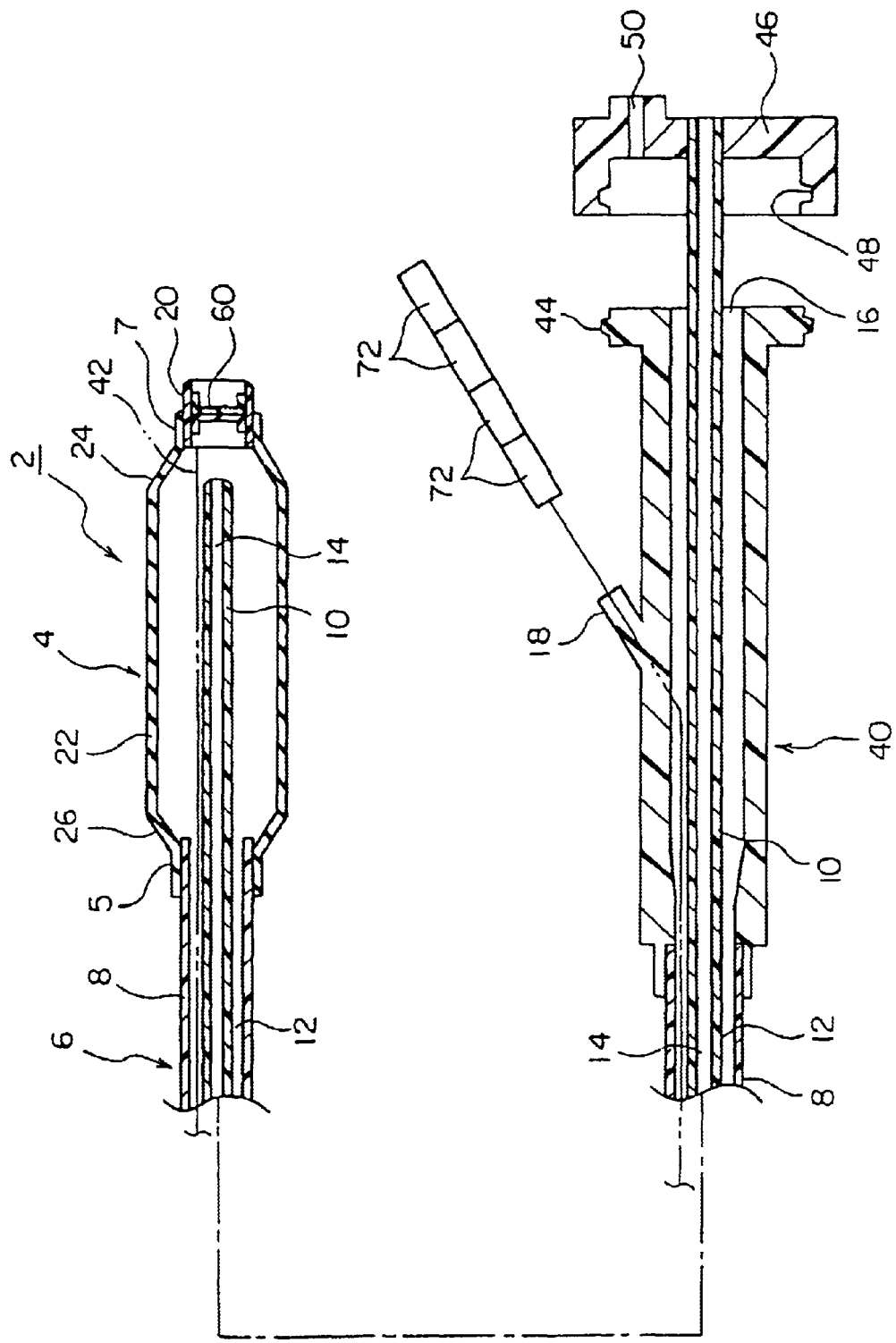
FIG. 2 is a sectional view of key parts showing the state of use of the balloon catheter shown in FIG. 1.
Figure 5:
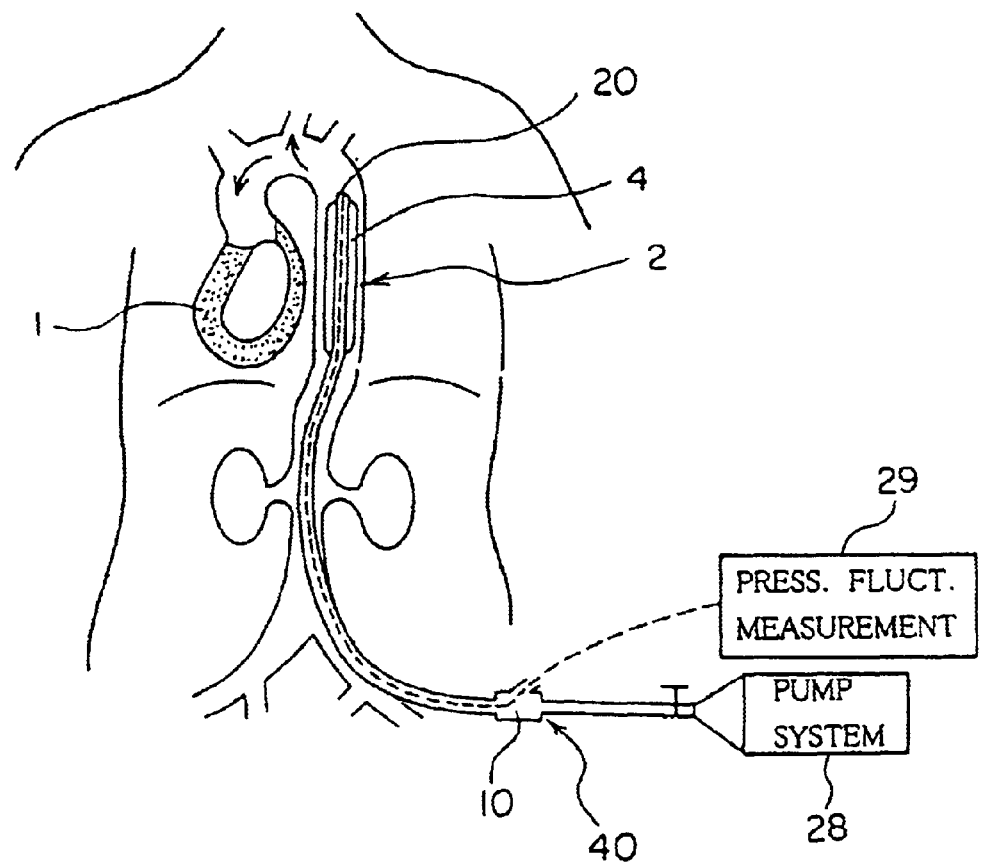
FIG. 5 is a schematic view of the state after inserting the balloon catheter according to the present embodiment into the blood vessel.

Next, the dilator is pulled out from the introducer 35 and then the proximal end of the guidewire 34 is inserted from the balloon portion 4 of the balloon catheter 2 shown in FIG. 1 into the inside of the second lumen 14 of the inner tube 10 and the balloon catheter 2 is inserted into the introducer 35, so that the balloon catheter 2 is adroitly inserted into the blood vessel 32 along the guidewire 34. Further, as shown in FIG. 5, in the state with the front end of the balloon portion 4 positioned in the blood vessel close to the heart 1, first, the guidewire 34 shown in FIG. 4 is pulled out from the blood vessel 32, then, as shown in FIG. 2, the cap 46 is detached from the port 16 of the connector 40 positioned outside the body, the inner tube 10 is pulled out along the longitudinal direction, and the connection between the valve element 60 of the front tip portion 20 and the distal end of the inner tube 10 is released. The valve element 60 ensures the seal of the inside of the balloon portion 4 even when the inner tube 10 is pulled out. Further, by pulling the cap 46, it is possible to pull the inner tube 10 out along the first lumen 12 of the outer tube 8. As a result, the inner tube 10 can be completely pulled out from the port 16, so that no inner tube 10 exists in the inside of the balloon portion 4 and the outer tube 8.

In this state, a pump device 28 shown in FIG. 5 is connected to the port 16 of the connector 40 shown in FIG. 2. The pump device 28 is used to pass shuttle gas through the port 16 shown in FIG. 1 and the first lumen 12 from which the inner tube 10 has been removed so as to introduce it into or release it from the inside of the balloon film 22. The shuttle gas introduced is not particularly limited, but helium gas, which has low viscosity and a small mass, may be used so that the balloon film 22 expands or contracts quickly in accordance with the drive operation of the pump device 28. Further, as the pump device 28, for example the device shown in Japanese Examined Patent Publication (Kokoku) No. 2-39265 may be used.

The terminal 72 led out from the connector 40 shown in FIG. 1 is connected to a blood pressure fluctuation measurement apparatus 29 shown in FIG. 5 and enables measurement of fluctuations in the blood pressure in the artery detected by the pressure sensor 70 shown in FIG. 3. Based on the fluctuations in the blood pressure measured by the blood pressure measurement apparatus 29, the pump device 28 is controlled in accordance with the beating of the heart 1 shown in FIG. 5 to cause expansion and contraction of the balloon portion 4 in the short period of 0.4 to 1 second and assist the heart 1.

In the balloon catheter 2 according to the present embodiment, when inserting the balloon catheter 2 into the blood vessel 32 of the patient, since the inner tube 10 is attached inside the balloon portion 4 and the outer tube 8 along the axial direction, by passing the guidewire 34 inside the second lumen 14 of the inner tube 10, it is possible to adroitly guide the balloon portion 4 of the balloon catheter 2 to a predetermined position inside the blood vessel 32.

As shown in FIG. 5, after positioning the balloon portion 4 at a predetermined position close to the heart 1 in the blood vessel 32, by pulling out the inner tube 10 from the proximal end side of the connector 40 positioned at the outer body side of the balloon catheter 2, no inner tube 10 exists inside the outer tube 8 forming the catheter tube 6. Around this time, the guidewire 34 is also pulled out from the proximal end side of the connector 40.

In the present embodiment, the cross-sectional area of the flow channel of the first lumen 12 of the outer tube 8 forming the catheter tube 6 becomes larger by the amount of the removal of the inner tube 10. As a result, the sectional area of the flow channel for feeding shuttle gas inside the balloon portion 4 by driving the pump system 28 shown in FIG. 5 becomes larger and the response of the expansion and contraction of the balloon portion 4 is remarkably improved. Further, this means that even if the outer diameter of the outer tube 8 forming the catheter tube 6 is made smaller than a conventional balloon catheter, a response characteristic of expansion and contraction of the balloon portion 4 equal to or better than that of the prior art is obtained. If the outer diameter of the outer tube 8 forming the catheter tube 6 can be made smaller, the discomfort to the patient can be alleviated.

Second Embodiment

Figure 7A:
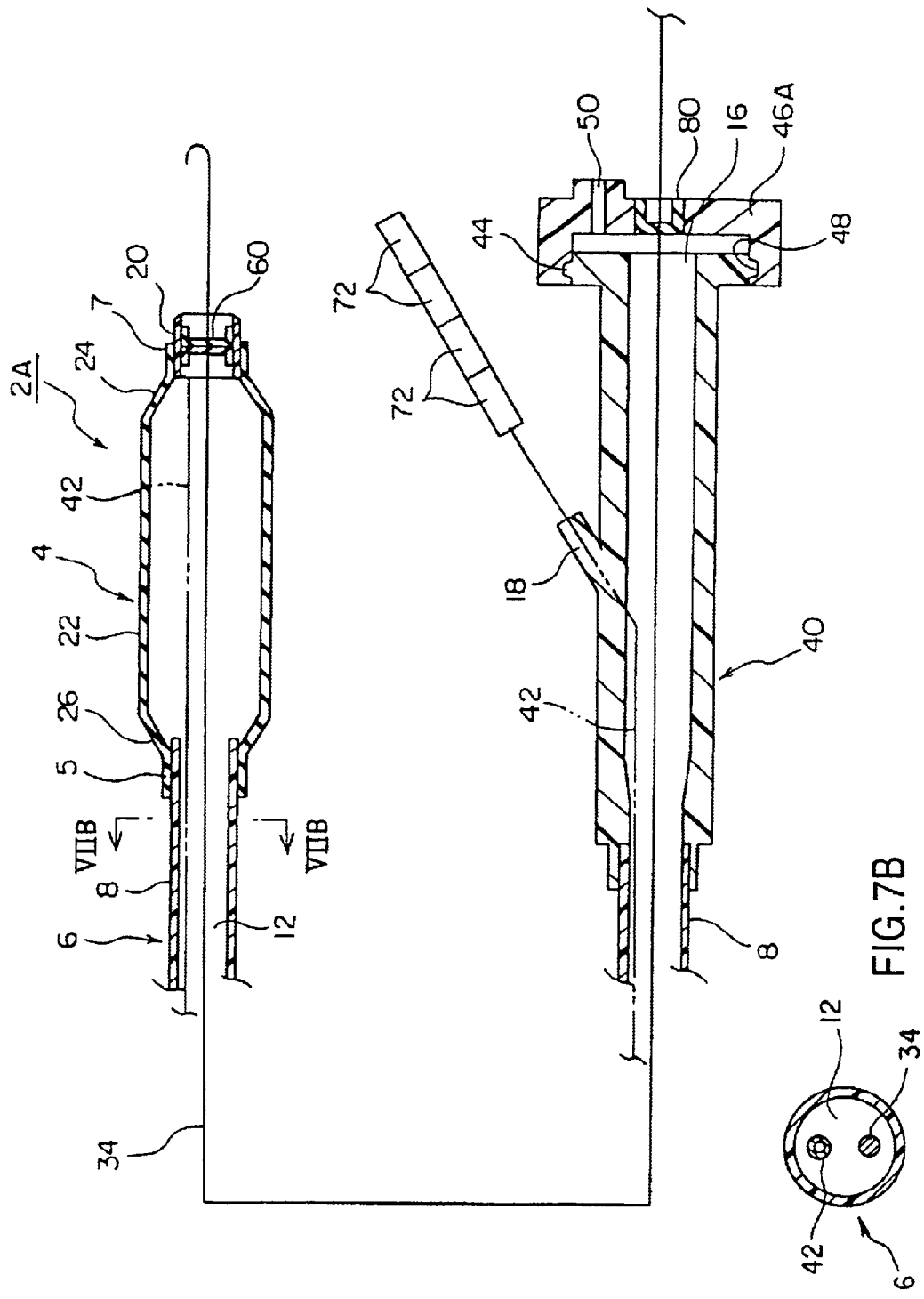
FIG. 7A is a schematic sectional view of a balloon catheter according to another embodiment of the present invention.
Figure 7B:
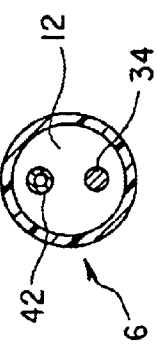
FIG. 7B is a sectional view along BVII—BVII shown in FIG. 7A.
Figure 9:
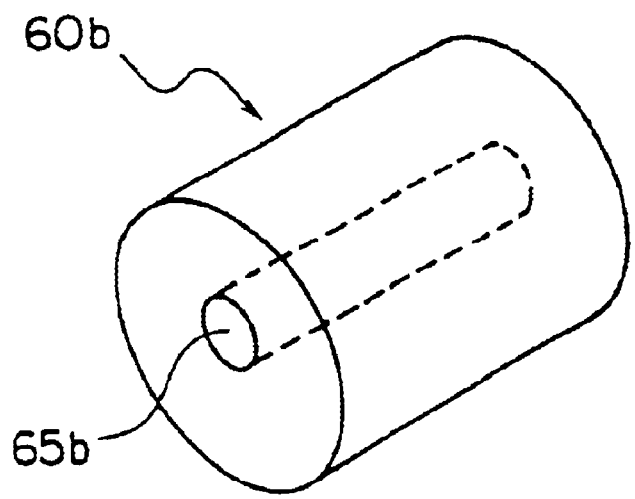
FIG. 9 is a perspective view of the valve element shown in FIG. 8C.

The balloon catheter 2A according to the second embodiment shown in FIG. 7 is used for IABP in the same way as the case of the first embodiment, but unlike the balloon catheter 2 of the first embodiment, there is no inner tube 10 attached from the start. Since no inner tube 10 is attached, a valve element 80 is attached to the center of the cap 46A without the inner tube. The guidewire 34 is detachably passed through this valve element 80. In both the state with the guidewire 34 attached and the state removed, the inside of the connector 40 is sealed from the outside. This valve element 80 is preferably a check valve. When introducing negative pressure from the negative pressure introduction port 50 to make the inside of the balloon portion 4 a negative pressure, there is at least a sealing action with the outside.

In the balloon catheter 2A according to the present embodiment, since no inner tube is attached from the very start, when inserting the balloon catheter 2 inside a blood vessel 32 of the patient, by passing the guidewire 34 along the inside of the first lumen 12 of the outer tube 8 and the balloon portion 4, it is possible to adroitly guide the balloon portion 4 of the balloon catheter 2 to a predetermined position in the blood vessel 32. Next, the guidewire 34 is pulled out from the proximal end side of the connector 40, the cap 46A is removed from the connector 40, the pump device 28 shown in FIG. 5 is connected to the port 16 of the connector 40, and the balloon catheter 2A is used for treatment. In this state, the balloon catheter 2A of this embodiment is used in the same state as the balloon catheter 2 of the first embodiment.

The rest of the configuration and actions are the same as with the balloon catheter of the first embodiment. In this embodiment as well, the cross-sectional area of the flow channel of the first lumen 12 of the outer tube 8 forming the catheter tube 6 becomes larger by the amount of the elimination of the inner tube 10. As a result, the cross-sectional area of the flow channel for feeding shuttle gas inside the balloon portion 4 by driving the pump system 28 shown in FIG. 5 becomes larger and the response of the expansion and contraction of the balloon portion 4 is remarkably improved. Further, this means that even if the outer diameter of the outer tube 8 forming the catheter tube 6 is made smaller than that of a conventional balloon catheter, an equal or better response of expansion and contraction of the balloon portion 4 is obtained. If the outer diameter of the outer tube 8 forming the catheter tube 6 is made smaller, the discomfort to the patient can be alleviated.

Third Embodiment

Figure 6:
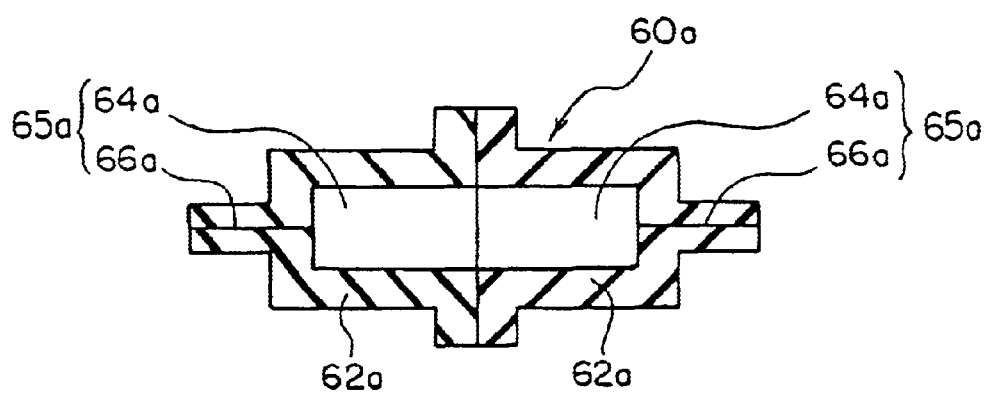
FIG. 6 is a schematic sectional view of a valve element used in the balloon catheter according to another embodiment of the present invention.

In this embodiment, instead of the valve element 60 attached to the inside of the front tip portion 20 shown in FIG. 3, as shown in FIG. 6, use is made of a valve element 60a comprised of so-called duckbill valves 62a, 62b combined back to back.

Each duckbill valve 62a has a tight-fit hole 65a comprised of a through hole 64a and a open-closable slit portion 66a. In both the state with the inner tube 10 inserted into the slit portion 66a and the state with it not inserted, it is possible to prevent circulation of fluid from the slit portion 66a side to the through hole 64a side.

By attaching the valve 60a comprised of such a pair of duckbill valves 62a and 62a, it is possible to obtain a valve action the same as that of the above valve element 60.

Fourth Embodiment

In this embodiment, instead of the valve element 60 attached to the inside of the front tip portion 20 of the balloon catheter 2A shown in FIG. 7A, use is made of the valve element 60b shown in FIGS. 8A to 8C and FIG. 9. This valve element 60b is shaped overall as a cylinder and is formed along its axial core with a tight-fit hole 65b comprised of a through hole with a substantially circular cross-section.

As shown in FIG. 8C, in the state before the valve element 60b is attached to the inside of the front tip portion 20, the outer diameter D2 of the valve element 60b is larger than the inside diameter D of the front tip portion 20. As shown in FIG. 8A, the valve element 60b is compressed and elastically deformed to the inside of the front tip portion 20 and attached there in a state with the tight-fit hole 65b closed.

The tight-fit hole 65b is preferably formed in a state before the valve element 60b is attached to the inside of the front tip portion 20, but may also be formed after being attached to the inside of the front tip portion 20. Whatever the case, as shown in FIG. 8A, in the state with the valve element 60b attached to the inside of the front tip portion 20, the tight-fit hole 65b is closed and the inside of the balloon portion 4 is sealed. The tight-fit hole 65b may be formed integrally at the time of molding the valve element 60b, but may also be formed after molding the valve element 60b by a needle or other tool. The tight-fit hole 65b, as shown in FIG. 8B, has the guidewire 34 inserted through it, so the tight-fit hole 65b may also be coated with silicone oil or another lubricant.

In FIG. 8C, the tight-fit hole 65b formed in the valve element 60b is clearly illustrated in a state before the valve element 60b is attached to the inside of the front tip portion 20, but in actuality since the hardness of the polymer material forming the valve element 60b is considerably low, the tight-fit hole 65b is almost completely blocked due to deformation. The outer diameter D3 of the needle or other tool for forming the tight-fit hole 65b is an outer diameter of about D4 ×0.3 to D4×1.0 when the outer diameter of the guidewire 34 is D4. The tight-fit hole 65b formed by the tool is, directly after formation, almost completely blocked by deformation at the stage before the element is attached to the inside of the front tip portion 20.

As shown in FIG. 8C, in the state before the valve element 60b is attached to the inside of the front tip portion 20, the outer diameter D2 of the valve element 60b is larger than the inside diameter D1 of the front tip portion 20. At a maximum, it is preferably larger than 2.0 times the same. In this range, by making the outer diameter D2 larger than the inside diameter D1, the valve element 60b is deformed well by compression and fit inside the front tip portion 20 to completely close the tight-fit hole 65b.

The axial length L1 of the valve element 60b is not particularly limited so longer as it is shorter than the axial length L2 of the front tip portion 20, as shown in FIG. 8C, in the state before the valve element 60b is attached to the inside of the front tip portion 20, but preferably is a length of about 5 to 95% the length L2.

The valve element 60b of the present embodiment, as shown in FIG. 8A, is compressed to deform and fit inside the front tip portion 20 and further, as shown in FIG. 8B, has the guidewire 34 inserted through it through the tight-fit hole 65b.

Therefore, the valve element 60b is preferably made of a material which is low in hardness, large in breaking elongation, and low in compression modulus of elasticity.

The Shore A hardness of the valve element 60b is preferably, based on JIS K6253, not more than 30, more preferably not more than 20, particularly preferably not more than 15 and may be even not more than 5. If the Shore A hardness of the valve element 60b is larger than 30, in the state shown in FIG. 8A, the tight-fit hole 65bis not completely closed and the seal tends to be incomplete. Further, in the state shown in FIG. 8B, the tight-fit hole 65b easily splits due to insertion of the guidewire 34.

Further, the breaking elongation of the valve element 60b is preferably 300 to 1000%, more preferably 500 to 800%. The breaking elongation is measured based on JIS K7311. If the breaking elongation of the valve element 60b is smaller than 300%, in the state shown in FIG. 8B, the tight-fit hole 65b easily splits by insertion of the guidewire 34. Production of a valve element 60b with the breaking elongation larger than 1000% is difficult.

Further, the compression modulus of elasticity of the valve element 60b is preferably 0.01 to 0.30 kg/cm$^2$, more preferably 0.05 to 0.15 kg/cm$^2$. The compression modulus of elasticity is measured based by JIS K7208. If the compression modulus of elasticity of the valve element 60b is larger than 0.30 kg/cm$^2$, in the state shown in FIG. 8B, the resistance at the time of insertion of the guidewire 34 tends to become higher. Production of the valve element 60b with the compression modulus of elasticity larger than 0.01 kg/cm$^2$ is difficult.

As specific materials of the valve element 60b having such physical properties, a silicone rubber, polyurethane, polyacrylate, polyacrylamide, etc. may be mentioned, but a polyurethane and silicone are preferable, particularly silicone is preferable. This is because silicone is superior in properties such as heat resistance, resistance to absorption of water, sliding with the guidewire, and recovery (small stress relaxation). As the silicone, there are disassociated type silicone, single-liquid type silicone, addition-type two-liquid mixed type silicone, etc., but addition-type two-liquid mixed type silicone is preferable. This is because addition type two-liquid mixed type silicone has a small precipitation of the low molecular weight component, is relatively easy to manufacture, and is particularly preferable for medical use.

When using silicone, polyurethane, etc. as the material forming the valve element 60b, the hardness is adjusted to the above range by adjusting the ratio of weight of the curing agent to the main ingredients, the heating temperature and heating time at the time of molding, etc. When using a polyacrylate resin, polyacrylamide resin, etc. as the material forming the valve element 60b, the hardness is adjusted to the above range by the cross-linking conditions.

The valve element 60b is preferably sterilized before attachment to the balloon catheter or after attachment. As the sterilization, gas sterilization or electron beam sterilization may be mentioned.

As shown in FIG. 8A and FIG. 8B, the front tip portion 20 has attached inside it stopper members 90 and 92 positioned at both sides of the valve element 60b in the axial direction. The stopper members 90 and 92 are respectively ring shaped and are formed with through holes 91 and 93 allowing passage of the guidewire 34. The stopper members 90 and 92 are for preventing the valve element 60b from popping out from the inside of the front tip portion 20 along the axial direction and are made of a material at least harder than the valve element 60b. The members forming the stopper members 90 and 92 are not particularly limited, but ones of a polyurethane resin, epoxy resin, etc. may be mentioned.

The stopper members 90 and 92 may be affixed to the inside of the front tip portion 20 using an adhesive, but may also be simply fit there so as not to easily move in the axial direction. Further, they may be formed integrally so long as formed integrally with the front tip portion 20.

As shown in FIG. 8A, the distance in the axial direction between the two stopper members 90 and 92 is determined so that excess clearances 94 and 96 are formed with the valve element 60b positioned between them. The excess clearances 94 and 96, as shown in FIG. 8B, are clearances for allowing the tight-fit hole 65b to stretch and the valve element 60b to elastically deform in the axial direction in the state with the distal end of the guidewire 34 inserted in the tight-fit hole 65b of the valve element 60b. If the excess clearances 94 and 96 are too small, the resistance when inserting the guidewire 34 through the tight-fit hole 65b tends to become too great and the usage is worse. The magnitudes of the excess clearances 94 and 96, as shown in FIG. 8B, are determined based on the amount of elastic deformation of the valve element 60b in the axial direction in the state with the distal end of the guidewire 34 inserted through the tight-fit hole 65b of the valve element 60b.

In the present embodiment, the front tip portion 20 is preferably made of a member which can elastically deform to the outside in the radial direction. The reason is, as shown in FIG. 8B, that the tight-fit hole 65b stretches and the valve element 60b tries to stretch to the outside in the radial direction as well in the state with the distal end of the guidewire 34 inserted through the tight-fit hole 65b of the valve element 60b. Even if the front tip portion 20 is made of a material which will not stretch outward in the radial direction, there is no problem in that the valve element 60b is made of a material which easily elastically deforms in the axial direction.

However, by forming the front tip portion 20 by a member which can elastically deform to the outside in the radial direction, the resistance when inserting the distal end of the guidewire 34 through the tight-fit hole 65b of the valve element 60b becomes further smaller so this is more preferable. From this viewpoint, the front tip portion 20 is preferably made of a synthetic resin of the Shore A hardness, measured based on JIS K6253, of preferably about 40 to 95. In particular, the front tip portion is preferably made of a polyurethane which is superior in durability and resistance to thrombus. The hardness of the front tip portion 20 is made the above range since when the hardness of the front tip portion 20 is too low, the function of supporting the distal end of the balloon portion 4 tends to decline, while if the hardness is too high, the elastic deformation to the outside in the radial direction tends to become smaller.

With a balloon catheter having a valve element 60b according to the present embodiment inside the front tip portion 20, both in the state with the guidewire 34 passed through the inside of the front tip portion 20 as shown in FIG. 8B and in the state with the guidewire 34 not passed through it as shown in FIG. 8A, the inside of the balloon portion 4 is sealed well by the valve element 60b.

Note that the inner diameter D1 of the front tip portion 20 is relatively small, so it is difficult in practice to attach a conventional slitted valve element inside the front tip portion 20 as it is. The reason is that with a conventional slitted valve element, the element easily breaks from the slit portion and slitting is difficult. The valve element 60b of the present embodiment only has the tight-fit hole 65b of the simple through hole shape, so is small in size, easy to produce, and reliable in sealing.

Figure 10:
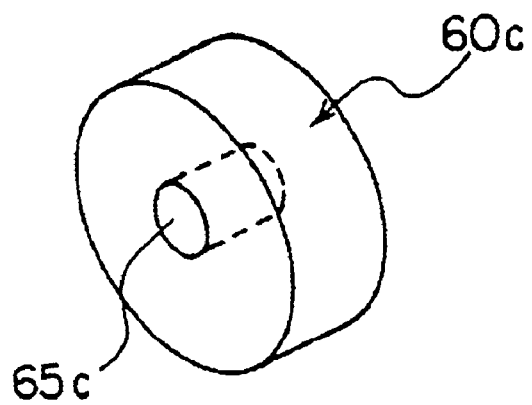
FIG. 10 to FIG. 14 are perspective views of other examples of valve elements.

Further, in the present invention, instead of the cylindrically shaped valve element 60b, use may be made of the valve elements 60c to 60g of the shapes shown in FIG. 10 to FIG. 14. The valve element 60c shown in FIG. 10 is a disk shaped valve element. Other than the difference in shape, it is similar to the valve element 60b shown in FIG. 8 and FIG. 9 and has a tight-fit hole 65c similar to the tight-fit hole 65b.

Figure 11:
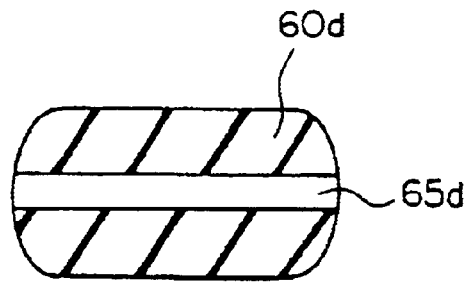
Figure 12:
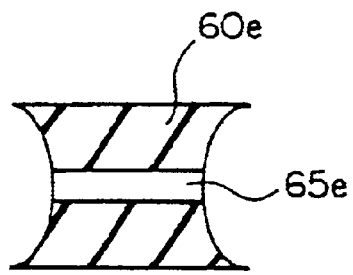
Figure 13:
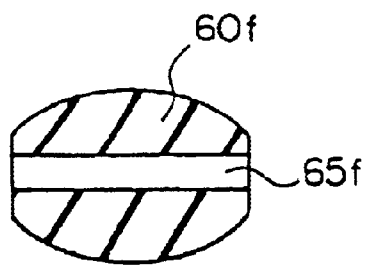
Figure 14:
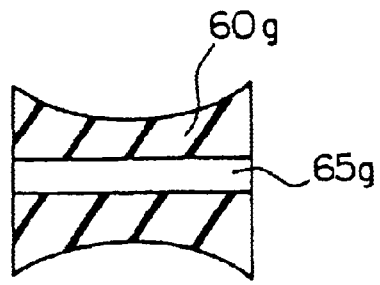

The valve element 60d shown in FIG. 11 is a valve element shaped as a cylinder with two convex end faces. Other than the difference in shape, it is similar to the valve element 60b shown in FIG. 8 and FIG. 9 and has a tight-fit hole 65d similar to the tight-fit hole 65b. The valve element 60e shown in FIG. 12 is a valve element shaped as a cylinder with two concave end faces. Other than the difference in shape, it is similar to the valve element 60b shown in FIG. 8 and FIG. 9 and has a tight-fit hole 65e similar to the tight-fit hole 65b. The valve element 60f shown in FIG. 13 is a valve element shaped as a cylinder with a convex outer circumference. Other than the difference in shape, it is similar to the valve element 60b shown in FIG. 8 and FIG. 9 and has a tight-fit hole 65f similar to the tight-fit hole 65b. The valve element 60g shown in FIG. 14 is a valve element shaped as a cylinder with a concave outer circumference. Other than the difference in shape, it is similar to the valve element 60b shown in FIG. 8 and FIG. 9 and has a tight-fit hole 65g similar to the tight-fit hole 65b.

The valve element used for the balloon catheter according to the present invention may be a valve element shaped as shown: in FIG. 9 to FIG. 14 or a valve element of a combination of these shapes.

Note that the valve elements 60b to 60g of the configurations shown in the above FIG. 8 to FIG. 12 may also be used as hemostatic valves of medical devices other than balloon catheters.

Fifth Embodiment

Figure 15A:
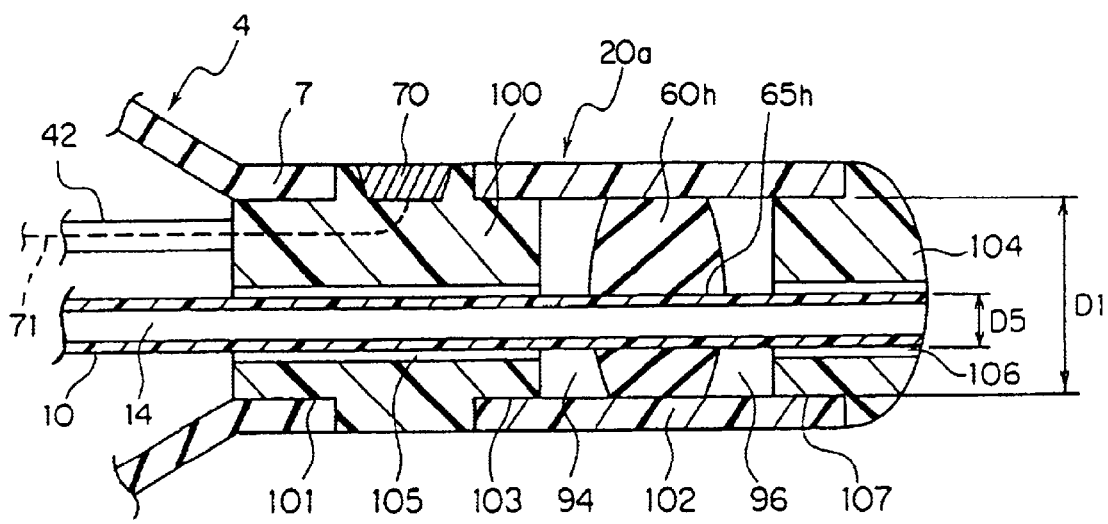
FIG. 15A is a schematic sectional view of key parts of a balloon catheter according to another embodiment of the present invention.
Figure 15B:
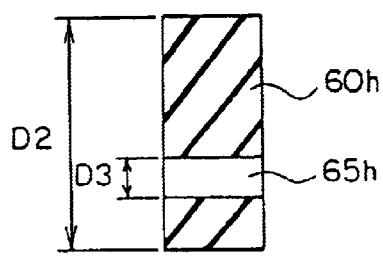
FIG. 15B is a sectional view of key parts shown in FIG. 15A.

In the present embodiment, instead of the front tip portion 20 and valve element 60 of the balloon catheter 2 shown in FIG. 1A and FIG. 2, use is made of the front tip portion 20a shown in FIG. 1SA and the valve element 60h shown in FIG. 15B.

The front tip portion 20a of the present embodiment is comprised of a sensor block 100 for holding the pressure sensor 70, a front tube 102, and a cap 104. A first cylindrical recess is formed in the outer circumference at the proximal end of the sensor block 100 in the axial direction. The extreme distal end 7 of the balloon portion 4 is heat bonded or adhered there. The distal end of the tube shaped supporting rod member 42 is joined to the end face of the proximal end of the sensor block 100 in the axial direction. Wires 71 from the pressure sensor 70 attached to the outer circumference of the sensor block extend inside the supporting rod member 42 in the axial direction. The pressure sensor 70 measures the blood pressure inside the blood vessel positioned at the outer circumference of the front tip portion 20a and outputs a signal through the wires 71 to the outside.

A second cylindrical recess 103 is formed at the outer circumference of the distal end of the sensor block 100 in the axial direction. The proximal end of the front tube 102 is heat bonded or adhered here. Further, an axial through hole 105 is formed at a position somewhat offset from the axial center of the sensor block 100. The distal end of the inner tube 10 is loosely inserted into this through hole 105. The inner diameter of the through hole 105 is preferably about 0.9 to 1.2 times the outer diameter D5 of the inner tube 10.

The distal end of the front tube 102 is heat bonded or adhered to a third cylindrical recess 107 formed in the back surface of the cap 104. The inner diameter and thickness of the front tip portion 102 are made about the same as the inner diameter and thickness of the front tip portion 20 shown in FIG. 1 to FIG. 3.

A convex curved surface is formed at the front surface of the cap 104 so as to lighten the resistance at the time of insertion of the balloon catheter, lower the discomfort to the patient, and improve the work efficiency at the time of insertion. The cap 104 is formed with an axial through hole 106 offset from the axial center in the same way as the through hole 105 of the sensor block 100. The through hole 106 has the distal end of the inner tube 10 loosely inserted into it. The axial center of the through hole 106 is substantially the same as the axial center of the through hole 105 and has a similar inner diameter.

The valve element 60h according to the present embodiment is a modification of the valve element 60c shown in FIG. 10 and is shaped overall as a disk and has a tight-fit hole 65h of a substantially circular cross-section formed somewhat offset from the axial center. As shown in FIG. 15A and FIG. 15B, the relationship between the outer diameter D2 of the tight-fit hole of the valve element 60h before attachment to the inside of the front tube 102 and the inner diameter D1 of the front tube 102 is similar to the relationship between the outer diameter D2 of the valve element 60b and the inner diameter D1 of the front tip portion 20 of the embodiment shown in FIG. 8A to FIG. 8C.

In FIG. 15B, the offset tight-fit hole 65h of the valve element 60h before attachment to the inside of the front tube 102 is clearly illustrated, but in fact since the hardness of the polymer material forming the valve element 60h is considerably low, the tight-fit hole 65h is almost completely blocked by deformation. The outer diameter D3 of the needle or other tool for forming the tight-fit hole 65h is an outer diameter of about D4×0.3 to D4×1.0 when the outer diameter of the inner tube 10 is D4. The tight-fit hole 65h formed by the tool is, immediately after formation, almost completely blocked by deformation at the stage before attachment of the element to the inside of the front tube 102.

The offset axial center of the tight-fit hole 65h formed in the valve element 60h substantially matches with the axial centers of the through holes 105 and 106. Note that the axial center of the tight-fit hole 65h is made offset since it is difficult to arrange the inner tube 10 along the center axis of the front tip portion 20a due to the supporting rod member 42.

The valve element 60h shown in FIG. 15B is deformed by compression and inserted to the inside of the front tube 102 shown in FIG. 15A. Therefore, in the state with the distal end of the inner tube 10 pulled out from the front tip portion 20a, the tight-fit hole 65h is collapsed and blocked and the inside of the balloon portion 5 is sealed from the outside.

In the present embodiment, the sensor block 100 and cap 104 forming the front tip portion 20a also serve as the stopper members 90 and 92 shown in FIG. 8A and FIG. 8B. Excess clearances 94 and 96 similar to the excess clearances 94 and 96 shown in FIG. 8A and FIG. 8B are formed at both sides of the valve element 60h in the axial direction.

The material and compression modulus of elasticity and other physical properties of the valve element 60h are similar to those of the valve element 60b shown in FIG. 8C, so explanations thereof will be omitted. Further, the balloon catheter according to the present embodiment differs from the balloon catheter of the embodiment shown in FIG. 1A and FIG. 2 only in the structure of the front tip portion 20a. The rest of the structure is the same and similar actions and effects as the above balloon catheter are exhibited.

In particular, in the balloon catheter of the present embodiment, the hardness of the front tube 102 and the cap 104 is made lower than the sensor block 100, that is, the pliability of the front tube 102 and the cap 104 is made higher than the sensor block 100, so as to improve the work efficiency in insertion of the balloon catheter. Further, it is possible to alleviate the discomfort to the patient at the time the balloon catheter is inserted into the blood vessel. From the above viewpoints, the front tube 102 and the cap 104 preferably are made of a synthetic resin such as polyurethane with the Shore A hardness of preferably 70 to 98, more preferably 80 to 95. As opposed to this, the sensor block 100 is preferably made of stainless steel, ceramic, or the like with the Shore D hardness of preferably at least 70.

Other Embodiments

Note that the present invention is not limited to the above embodiments and can be modified in various ways within the scope of the invention.

For example, the supporting rod member 42 does not necessarily have to be tubular in shape. For example, when the output signal from the pressure sensor 70 shown in FIG. 3 is transmitted over an optical fiber etc., the supporting rod member 42 may also be made of optical fiber etc.

Further, in the above embodiments, the balloon catheter according to the present invention was used for IABP, but it may also be used for other applications (for example, PTCA).

Further, in the present invention, the valve element which can be attached to the inside of the front tip portion 20 is not limited to those shown in FIG. 3, FIG. 6, FIG. 8 to FIG. 14, or FIG. 15B.

As explained above, according to the balloon catheter of the present invention, when feeding pressurized fluid to the balloon portion, the inner tube of the catheter tube is removed. Therefore, the cross-sectional area of the flow channel of the first lumen of the outer tube of the catheter tube becomes larger by the amount of removal of the inner tube. As a result, the cross-sectional area of the flow channel for feeding the pressurized fluid to the inside of the balloon portion becomes larger and the response in expansion and contraction of the balloon portion is remarkably improved. Further, this means that even if the outer diameter of the outer tube forming the catheter tube is made smaller than the conventional balloon catheter, an equal or better response of expansion and contraction of the balloon portion can be obtained. If the outer diameter of the outer tube of the catheter tube can be made smaller, the discomfort to the patient can be alleviated.

What is claimed is:

1. A balloon catheter comprising:
an outer tube having a first lumen inside the outer tube, a balloon portion having a proximal end joined to a distal end of the outer tube and a distal end of the balloon portion joined to a tubular shaped front tip portion axially spaced from said distal end of said outer tube, said front tip portion having a valve element sealing the balloon space inside the balloon portion from the outside of the balloon portion and being formed of a resilient material and operative to normally close the balloon portion in order to form a balloon space inside the balloon portion, into which a pressurized fluid is introduced and released through the first lumen of the outer tube to give an expanded and contracted state, an inner tube having a second lumen therein, said inner tube extending inside the first lumen of the outer tube and being mounted therein to freely slide in the axial direction, projecting out from the distal end of the outer tube, and said inner tube penetrating said front tip portion and being detachably attached thereto and effective to close said tip portion upon withdrawal of said inner tube therefrom to thereby close said balloon portion, wherein a distal end of the inner tube is detachably attached to the valve element for closing the valve element when the inner tube is withdrawn therefrom, wherein the valve element is formed with a tight-fit hole, a clearance with the inner tube is sealed in a state in which a distal end of the inner tube is inserted into the tight-fit hole, and the tight-fit hole being closeable upon withdrawal of said distal end of the inner tube to enable the balloon space at an inside of the balloon portion to be sealed from outside of the balloon portion in the state in which the inner tube, when detached from the tight-fit hole, closes the tight-fit hole to seal the balloon space, wherein a maximum outer diameter of the valve element is larger than an inside diameter of the front tip portion in a state before the valve element is attached to an inside of the front tip portion and wherein the valve element is compressed and elastically deformed to the inside of the front tip portion and is attached in the state with the tight-fit hole closed, wherein an extra clearance space for elastic deformation of the valve element in the axial direction is formed inside the front tip portion in order to widen the tight-fit hole in a state in which a distal end of the inner tube is inserted into the tight-fit hole of the valve element, and wherein the front tip portion has stopper members positioned at both sides of the valve element in the axial direction to create the extra clearance space inside the front tip portion and the stopper members are constructed to allow passage of the inner tube.

2. The balloon catheter as set fort in 1, wherein the valve element has a Shore A hardness of not more than 30.

3. The balloon catheter as set forth in claim 1, wherein the valve element has a breaking elongation of 300 to 1000%.

4. The balloon catheter as set forth in claim 1, wherein the valve element has a compression modulus of elasticity of 0.01 to 0.30.

5. The balloon catheter as set forth in claim 1, wherein the front tip portion is comprised of a member which can elastically deform outwardly in the radial direction.

6. The balloon catheter as set forth in claim 1, wherein the front tip portion is provided with a pressure sensor.

7. The balloon catheter as set forth in claim 1, further comprising a supporting rod member having a distal end joined to the front tip portion and extending inside the balloon portion and the outer tube in the axial direction separate from the inner tube.

8. The balloon catheter as set forth in claim 7, wherein the supporting rod member is comprised of a tube and inside the tube is passed or buried wiring from the pressure sensor.

9. The balloon catheter as set forth in claim 1, wherein the proximal end of the outer tube is connected to a connector and the proximal end of tie guidewire is detachably attached to the connector.

10. The balloon catheter as set forth in claim 9, wherein the proximal end of the supporting rod member is connected to the connector.

11. A method of using the balloon catheter constructed according to claim 1 wherein the catheter is used for intra aortic balloon pumping (IABP).

12. A balloon catheter comprising;
an outer tube having a first lumen inside the outer tube, a balloon portion having a proximal end joined to a distal end of the outer tube and a distal end of the balloon portion joined to a tubular shaped front tip portion which is axially spaced from the distal end of the outer tube, the front tip portion capping the distal end of the balloon portion in order to form a balloon space inside the balloon portion, into which a pressurized fluid is introduce into, and released from, through the first lumen of the outer tube to give the balloon portion an expanded and contracted state, and a guidewire extending inside the first lumen of the outer tube to be freely slidable in the axial direction, the front tip portion providing a valve element through which the guidewire is passed in a detachable manner, the valve element being separate from said tip portion and being attached thereto so as to maintain an inside of the balloon portion sealed in both a state in which the guidewire is attached and a state in which the guidewire is not attached to the valve element, wherein the valve element is formed with a tight-fit hole, a clearance between the guidewire and said hole in the valve element when the distal end of the guidewire is inserted into the tight-fit hole, and the tight-fit hole closes to enable the balloon space at an inside of the balloon portion to be sealed from outside of the balloon portion when the guidewire is a detached from the tight-fit hole, wherein the valve element is formed of a resiliently compressable material having a maximum outer diameter larger than an inside diameter of the front tip portion in a state before the valve element is attached to an inside of the front tip portion, and wherein the valve element is compressed and elastically deformed to the inside of the front tip portion to be attached in a state in which the tight-fit bole is closed, and wherein an extra clearance space for elastic deformation of the valve element in the axial direction is formed inside the front tip portion in order to widen the tight-fit hole in a state in which a distal end of the guidewire is inserted into the tight-fit hole of the valve element wherein the front tip portion has stopper members positioned at both sides of the valve element in the axial direction to create the extra clearance space inside the front tip portion, the stopper members being constructed to allow passage of the guidewire.

13. The balloon catheter as set forth in claim 12, wherein the valve element has a Shore A hardness of not more than 30.

14. The balloon catheter as set forth in claim 12, wherein the valve element has a breaking elongation of 300 to 1000%.

15. The balloon catheter as set forth in claim 12, wherein the valve element has a compression modulus of elasticity of 0.01 to 0.30 kg/cm$^2$.

16. The balloon catheter as set forth in claim 12, wherein the front tip portion is comprised of a member which can elastically deform outwardly in the radial direction.

17. The balloon catheter as set forth in claim 12, wherein the front tip portion is provided with a pressure sensor.

18. The balloon catheter as set forth in claim 12, further comprising a supporting rod member having a distal end joined to the front tip portion and extending inside the balloon portion and the outer tube in the axial direction separate from the inner tube.

19. The balloon catheter as set forth in claim 18, wherein the supporting rod member is comprised of a tube and inside the tube is passed or buried wiring from the pressure sensor.

20. The balloon catheter as set forth in claim 12, wherein the proximal end of the outer tube is connected to a connector and the proximal end of the guidewire is detachably attached to the connector.

21. The balloon catheter as set forth in claim 20, wherein a proximal end of a supporting rod member is connected to the connector.

22. A method of using the balloon catheter constructed according to claim 12, wherein the catheter is used for intra aortic balloon pumping (LABP).

* * * * *